United States Patent
Ohkawara

(10) Patent No.: US 9,018,235 B2
(45) Date of Patent: *Apr. 28, 2015

(54) INSECTICIDE COMPOSITIONS

(75) Inventor: Yuichi Ohkawara, Kawanishi (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/788,679

(22) Filed: May 27, 2010

(65) Prior Publication Data

US 2010/0227893 A1 Sep. 9, 2010

Related U.S. Application Data

(62) Division of application No. 10/590,309, filed as application No. PCT/JP2005/002708 on Feb. 21, 2005.

(30) Foreign Application Priority Data

Feb. 24, 2004 (JP) .................. 2004-048376
May 27, 2004 (JP) .................. 2004-158349

(51) Int. Cl.
*A01N 43/40* (2006.01)
*A01P 7/04* (2006.01)
*A01N 43/56* (2006.01)

(52) U.S. Cl.
CPC ...................... *A01N 43/56* (2013.01)

(58) Field of Classification Search
CPC ... A01N 43/56; A01N 2300/00; A01N 47/40; A01N 51/00
USPC ........................................ 514/341
See application file for complete search history.

(56) References Cited

U.S. PATENT DOCUMENTS

| | | | |
|---|---|---|---|
| 7,696,232 B2 * | 4/2010 | Berger et al. ............... | 514/341 |
| 8,101,772 B2 | 1/2012 | Wachendorff-Neumann et al. | |
| 2004/0198984 A1 | 10/2004 | Lahm et al. | |
| 2007/0232598 A1 | 10/2007 | Funke et al. | |

FOREIGN PATENT DOCUMENTS

| | | | | |
|---|---|---|---|---|
| CA | 2454485 A1 * | 2/2003 | ............ | A01N 43/56 |
| CA | 2 545 586 | 6/2005 | | |
| JP | 2001-081003 | 3/2001 | | |
| JP | 2003-55115 | 2/2003 | | |
| JP | 2003-321310 | 11/2003 | | |
| JP | 2004-043436 | 2/2004 | | |
| WO | 03/015515 | 2/2003 | | |
| WO | 03/015518 | 2/2003 | | |
| WO | 03/015519 | 2/2003 | | |
| WO | WO 03015519 A1 * | 2/2003 | | |
| WO | 03/024222 | 3/2003 | | |
| WO | WO 03024222 A1 * | 3/2003 | | |
| WO | 03/027099 | 4/2003 | | |
| WO | 2004/046129 | 6/2004 | | |
| WO | WO 2004046129 A2 * | 6/2004 | | |
| WO | 2005/048711 | 6/2005 | | |

OTHER PUBLICATIONS

International Search Report mailed Apr. 19, 2005 in International (PCT) Application No. PCT/JP2005/002708.
Supplementary European Search Report issued Aug. 23, 2010 in corresponding European Application No. 05 71 9327, in the English language.
Takashi Kidokoro, "Present State and Prospect of Pesticides for Nursery Boxes for Paddy Rice", Special Issue of Agriculture of this month, Dec. 2001, pp. 118-123, with partial English translation.
Canadian Office Action issued Dec. 15, 2011 in corresponding Canadian Patent Application No. 2,556,300.

* cited by examiner

*Primary Examiner* — Janet Epps-Smith
*Assistant Examiner* — Courtney Brown
(74) *Attorney, Agent, or Firm* — Wenderoth, Lind & Ponack, L.L.P.

(57) ABSTRACT

Insecticide compositions which comprise one or not less than two kinds of compounds being selected from a compound represented by the formula [I]:

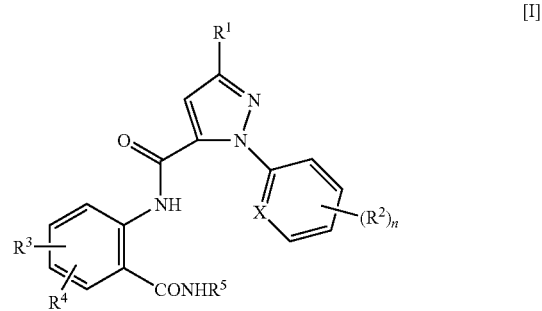

or a salt thereof, and a neonicotinoid compound represented by the formula [II]:

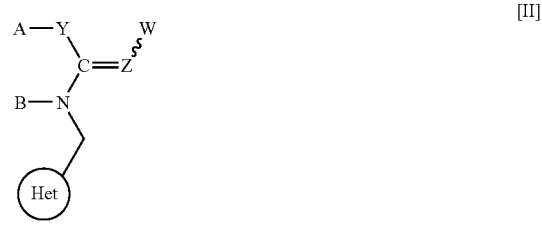

The insecticide compositions can produce higher insecticidal effects than would be expected when each of the active ingredients is used singly, namely a synergistic effect, thus enabling reductions in the rate or number of application of agrochemicals and pesticides to be realized.

2 Claims, No Drawings

INSECTICIDE COMPOSITIONS

This application is a divisional application of U.S. application Ser. No. 10/590,309, filed Oct. 12, 2006, now pending, which is the national phase filing of International Patent Application Ser. No. PCT/JP2005/00278, filed Feb. 21, 2005.

TECHNICAL FIELD

The present invention relates to compositions exhibiting excellent inseciticidal action, which comprise the compounds represented by the general formula [I] or salts thereof and the neonicotinoid compounds represented by the general formula [II], and to methods for controlling insect pests by use of a mixture of said compounds.

BACKGROUND ART

The compounds represented by the general formula [I] which are usable in the present invention are the known compounds exhibiting insecticidal action (refer to Patent Literature Nos. 1, 2 and 3).

Also, the neonicotinoid compounds represented by the general formula [II], which are utilizable in the present invention, are the compounds known to have insecticidal action, and include, for example, the compounds described in Pesticide Manual, 12th edition (Non-Patent Literature No. 1), etc., such as clothianidin (chemical name: (E)-1-(2-chloro-1,3-thiazol-5-ylmethyl)-3-methyl-2-nitroguanidine; Non-Patent Literature No. 1, No. 165, page 197; Patent Literature No. 4), nitenpyram (chemical name: (E)-N-(6-chloro-3-pyridylmethyl)-N-ethyl-N'-methyl-2-nitrovinylidenediamine; Non-Patent Literature No. 1, No. 562, page 674; Patent Literature No. 5), imidacloprid (chemical name: 1-(6-chloro-3-pyridylmethyl)-N-nitroimidazolidin-2-ylideneamine; Non-Patent Literature No. 1, No. 446, page 537; Patent Literature No. 6), thiamethoxam (chemical name: 3-(2-chloro-1,3-thiazol-5-yl-methyl)-5-methyl-1,3,5-oxa-diazinan-4-ylidene(nitro)amine; Non-Patent Literature No. 1, No. 751, page 896; Patent Literature No. 7), acetamiprid (chemical name: (E)-N-[(6-chloro-3-pyridyl)methyl]-N'-cyano-N-methylacetamidine; Non-Patent Literature No. 1, No. 6, page 9; Patent Literature No. 8), dinotefuran (chemical name: (RS)-1-methyl-2-nitro-3-(tetrahydro-3-furylmethyl)guanidine; Non-Patent Literature No. 1, No. 265, page 319; Patent Literature No. 9), thiacloprid (chemical name: 3-(6-chloro-3-pyridylmethyl)-1,3-thiazolidin-2-ylidenecyanamide; CAS registry No. 111988-49-9; Patent Literature No. 10), and the like.

As examples of the compounds which can be incorporated into the compounds represented by the formula [I], there are indicated the neonicotinoid compounds as described above, together with a large number of other insecticides (Patent Literature Nos. 1 to 3), but no description is given on the working examples in which such compounds are put into practical use as a mixture with the neonicotinoid compounds.
Patent Literature No. 1; Pamphlet of WO 01/070671
Patent Literature No. 2; Pamphlet of WO 03/015519
Patent Literature No. 3; Pamphlet of WO 03/016284
Patent Literature No. 4; Gazette of JP-A-Hei 3-157308
Patent Literature No. 5; Gazette of JP-A-Hei 2-000171
Patent Literature No. 6; Gazette of JP-A-Sho 61-178981
Patent Literature No. 7; Gazette of JP-A-Hei 6-183918
Patent Literature No. 8; Gazette of JP-A-Hei 4-154741
Patent Literature No. 9; Gazette of JP-A-Hei 7-179448
Patent Literature No. 10; Gazette of JP-A-Sho 62-207266
Non-Patent Literature No. 1; Pesticide Manual, 12th Edition, British Crop Protection Council.

DISCLOSURE OF THE INVENTION

Problems to be Solved by the Invention

In recent years, the environmental pollution with a variety of chemical substances have been grasped as a global-scale problem, and the intensified social demand exists for suppressing the release of chemical substances into the environment to a minimum level. In the filed of agriculture, also, diverse studies have been conducted to exploit a method for controlling harmful and injurious organisms, or pests, without use of chemical substances, such as the creation or generation of genetically modified crops, the control of pests with their natural enemies and the physical control of pests, etc.

However, such methods for controlling pests without use of chemical substances are encountered with numerous problems, such as their uniquely limited, sole use in controlling specific diseases or insect pests, instability of the effect, and the like, and the need for controlling pests with chemical substances therefore has not yet been reduced.

Means for Solving the Problem

The present inventors, with a specific view to reduction in application rate of agricultural chemicals or pesticides from the standpoint of prevention of the environmental pollution, etc., conducted repeated intensive research, and as a result, found that a mixture of a compound represented by the general formula [I] with a neonicotinoid compound represented by the general formula [II] can produce a greater effect than would be expected when both of the compounds individually are applied solely, thus enabling a reduction in the rate or number of application of agrochemicals or pesticides to be realized. Also, it was found that such mixtures, even when applied to locations other than the sites on which insect pests inflict injuries directly, such as seeds, seed potatoes or soils of nursery beds or farms on which crops are grown, and the like, can control insect pests in an extremely effective manner. Such findings, followed by continued intensive investigation, led to completion of the present invention.

Namely, the present invention relates to:

[1] an insecticide composition which comprises one or not less than two kinds of compounds being selected from a compound represented by the formula [I]:

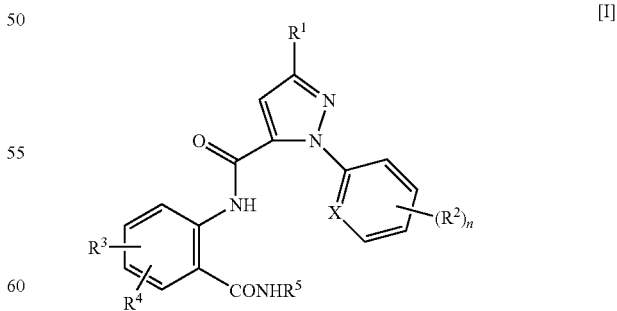

wherein $R^1$, $R^2$, $R^3$ and $R^4$ are the same or different, and each represent a hydrogen atom, a $C_{1-6}$ alkyl group, a $C_{1-6}$ haloalkyl group or a halogen atom; $R^5$ is a hydrogen atom or a $C_{1-6}$ alkyl group; X is CH or N; n is 0 to 3 or a salt thereof and a neonicotinoid compound represented by the formula [II]:

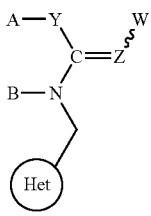

wherein Y is $CH_2$, S or $NR^6$ ($R^6$ is a hydrogen atom or a $C_{1-6}$ alkyl group); Z is N or CH; W is a cyano or nitro group; A and B are the same or different, and each represent a hydrogen atom or a $C_{1-6}$ alkyl group, or are taken together with the adjacent Y, C and N to form a ring represented by the formula:

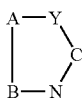

wherein the ring [A] is a group represented by the formula:

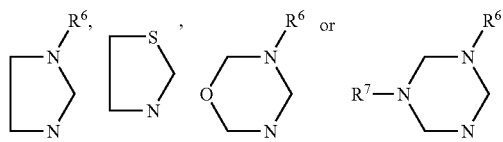

(wherein $R^6$ is as defined hereinbefore; $R^7$ is a hydrogen atom or a $C_{1-6}$ alkyl group), and the formula:

represents a heterocyclic group being selected from pyridyl, thiazolyl and tetrahydrofuryl groups, the said heterocyclic ring being optionally substituted by 1 to 3 of halogen atoms;

[2] an insecticide composition according to the above-mentioned [1], wherein the compound represented by the formula [I] is a compound represented by the general formula [Ia]:

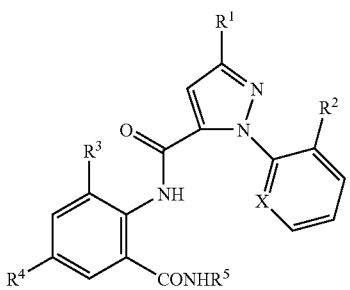

wherein the symbols are as defined hereinbefore;

[3] an insecticide composition according to the above-mentioned [2], wherein in the compound represented by the general formula [Ia], $R^1$ is a halogen atom or a $C_{1-6}$ haloalkyl group, $R^2$ is a halogen atom, $R^3$ and $R^5$ each are a $C_{1-6}$ alkyl group, $R^4$ is a hydrogen or halogen atom, and X is N;

[4] an insecticide composition according to the above-mentioned [2], wherein in the compound represented by the general formula [Ia], $R^1$ is a chlorine or bromine atom or a trifluoromethyl group, $R^2$ is a chlorine atom, $R^3$ is a methyl group, $R^5$ is an isopropyl group, $R^4$ is a hydrogen or chlorine atom, and X is N;

[5] an insecticide composition according to the above-mentioned [2], wherein the compound represented by the formula [Ia] is 2-[1-(3-chloropyridin-2-yl)-3-trifluoromethylpyrazol-5-ylcarbonylamino]-N-isopropyl-3-methylbenzamide, 5-chloro-2-[1-(3-chloropyridin-2-yl)-3-trifluoromethylpyrazol-5-ylcarbonylamino]-N-isopropyl-3-methylbenzamide, 2-[1-(3-chloro-pyridin-2-yl)-3-chloropyrazol-5-ylcarbonylamino]-N-isopropyl-3-methylbenzamide, 5-chloro-2-[1-(3-chloropyridin-2-yl)-3-chloropyrazol-5-ylcarbonylamino]-N-isopropyl-3-methylbenzamide, 2-[3-bromo-1-(3-chloropyridin-2-yl)pyrazol-5-ylcarbonylamino]-N-isopropyl-3-methylbenzamide or 2-[3-bromo-1-(3-chloro-pyridin-2-yl)pyrazol-5-ylcarbonylamino]-5-chloro-N-isopropyl-3-methylbenzamide;

[6] an insecticide composition according to any one of the above-mentioned [1] to [5], wherein the neonicotinoid compound represented by the formula [II] is clothianidin, nitenpyram, imidacloprid, thiacloprid, thiamethoxam, acetamiprid or dinotefuran;

[7] an insecticide composition as described in any one of the above-mentioned [1] to [5], wherein the neonicotinoid compound represented by the formula [II] is clothianidin;

[8] a method for controlling an insect pest, which comprises applying the insecticide composition as described in any one of the above-mentioned [1] to [7] to locations other than the site where the insect pest inflict injuries directly;

[9] a method for controlling an insect pest, characterized in that said method comprises mixing two kinds of the compounds, namely a compound represented by the general formula [I] or a salt thereof as described in anyone of the above-mentioned [1] to [7] and a neonicotinoid compound represented by the general formula [II], followed by drenching onto the soil for raising seedlings in the form of a mixture solution or application on the soil for raising seedlings in the form of a mixture granule, during the period ranging from the sowing time to the seedling-planting time for a crop to be cultivated by the seedling-planting method;

[10] a method for controlling an insect pest, characterized in that said method comprises raising seedlings with use of the soil for raising seedlings which has contained therein two kinds of the compounds, namely a compound represented by the general formula [I] or a salt thereof as described in any one of the above-mentioned [1] to [7] and a neonicotinoid compound represented by the general formula [II], during the period ranging from the sowing time to the seedling-planting time for a crop to be cultivated by the seedling-planting method;

[11] a method for controlling an insect pest, characterized in that said method comprises applying two kinds of the compounds, namely a compound represented by the general formula [I] or a salt thereof as described in any one of the above-mentioned [1] to [7] and a neonicotinoid compound represented by the general formula [II], to the soil of a farm field through drenching treatment, planting-hole treatment, planting-hole treated soil incorporation, plant-root treatment or plant-root treated soil incorporation during the period ranging from the seedling-planting time to the vegetation period for a crop to be cultivated by the seedling-planting method;

[12] a method for controlling an insect pest, characterized in that said method comprises effecting the soaking treatment, dusting treatment or coating treatment of a seed, seed potato or bulb with two kinds of the compounds, namely a compound represented by the general formula [I] or a salt thereof as described in any one of the above-mentioned [1] to [7] and a neonicotinoid compound represented by the general formula [II], in the case of a crop to be cultivated by directly sowing or seeding a seed, seed potato or bulb on the farm field; and

[13] a method for controlling an insect pest, characterized in that said method comprises applying two kinds of the compounds, namely a compound represented by the general formula [I] or a salt thereof as described in anyone of the above-mentioned [1] to [7] and a neonicotinoid compound represented by the general formula [II], to the soil of a farm field through drenching treatment, plant-root treatment or plant-root treated soil incorporation during the vegetation period of a crop to be cultivated by directly sowing or seeding a seed, seed potato or bulb on the farm field.

Effect of the Invention

A combination of a compound represented by the general formula [I] with a neonicotinoid compound represented by the general formula [II] can result in the development or elicitation of a higher insecticidal effect than would be expected when each of the compounds is applied solely, namely the synergistic effect, thus enabling reductions in the rate or number of application of agrochemicals to be realized.

BEST MODE FOR CARRYING OUT THE INVENTION

The compounds [I] or salts thereof and neonicotinoid compounds [II] in some instances exist in the forms of geometrical isomers and/or stereoisomers, and the present invention include such individual isomers and mixtures thereof.

Referring to the above-illustrated formulae, as the $C_{1-6}$ alkyl group represented by $R^1$ to $R^7$, for example, there is used methyl, ethyl, n-propyl, isopropyl, n-butyl, isobutyl, sec-butyl, or tert-butyl, etc.

As the $C_{1-6}$ haloalkyl group represented by $R^1$ to $R^4$, for example, there are used $C_{1-6}$ alkyl groups substituted by 1 to 10 (preferably 1 to 5) of halogen atoms (e.g., fluorine, chlorine, bromine, iodine), such as chloromethyl, fluoromethyl, bromomethyl, 2-chloroethyl, dichloromethyl, trichloromethyl, trifluoromethyl, 2,2,2-trifluoroethyl, pentafluoroethyl, heptafluoropropyl, or nonafluorobutyl, etc.

As the halogen atom represented by $R^1$ to $R^4$, there is used a fluorine, chlorine, bromine or iodine atom.

As $R^1$, halogen atoms and $C_{1-6}$ haloalkyl groups are particularly preferable, with chlorine and trifluoromethyl being more preferred.

As $R^2$, halogen atoms are preferred, with chlorine being particularly preferable. Their position of substitution preferably is the 2-position in the case of the mother cyclic group being a phenyl group, and the 3-position in the case of the mother cyclic group being a pyridyl group, respectively.

As $R^3$, a halogen atom and a $C_{1-6}$ group which are situated for substitution at the 3-position (the position of substitution refers to a position relative to 2-aminobenzoic acid used as a base nucleus) are preferable, with a 3-methyl group being particularly preferred.

As $R^4$, a hydrogen atom, and a halogen atom and a $C_{1-6}$ alkyl group which are situated for substitution at the 4- or 5-position (the position of substitution refers to a position relative to 2-aminobenzoic acid used as a base nucleus) are preferred, with a hydrogen atom and a 5-chlorine being particularly preferable.

As $R^5$, a $C_{1-6}$ alkyl group is preferred, with an isopropyl group being particularly preferable.

X represents CH or N, with N being particularly preferable.

n represents an integer of 0 to 3, with the integer of 1 being particularly preferable.

Y represents $CH_2$, S or $NR^6$, whereby as $R^6$, a hydrogen atom or a methyl group is preferred.

As $R^7$, a $C_{1-6}$ alkyl group is preferable, with a methyl group being particularly preferred.

As the group represented by the formula:

preferred is a 6-chloro-3-pyridyl, 2-chloro-5-thiazolyl or 3-tetrahydrofuryl group.

When Y is $CH_2$, then A preferably is a hydrogen atom, while B preferably is a methyl group.

When Y is S, then A and B preferably are taken together with the adjacent Y, C and N to form a ring.

When Y is $NR^6$, then A preferably is a hydrogen atom or a methyl group, while B preferably is a hydrogen atom, a methyl or ethyl group, and A and B preferably are taken together with the adjacent Y, C and N to form a ring, as well.

As the compound represented by the general formula [I], preferable are 2-[1-(3-chloropyridin-2-yl)-3-trifluoromethylpyrazol-5-ylcarbonylamino]-N-isopropyl-3-methylbenzamide, 5-chloro-2-[1-(3-chloropyridin-2-yl)-3-trifluoromethylpyrazol-5-ylcarbonylamino]-N-isopropyl-3-methylbenzamide, 2-[1-(3-chloropyridin-2-yl)-3-chloropyrazol-5-ylcarbonylamino]-N-isopropyl-3-methylbenzamide, 5-chloro-2-[1-(3-chloropyridin-2-yl)-3-chloropyrazol-5-ylcarbonylamino]-N-isopropyl-3-methylbenzamide, 5-chloro-2-[1-(3-chloropyridin-2-yl)-3-chloropyrazol-5-ylcarbonylamino]-N-isopropyl-3-methylbenzamide, 2-[3-bromo-1-(3-chloropyridin-2-yl) pyrazol-5-ylcarbonylamino]-N-isopropyl-3-methylbenzamide or 2-[3-bromo-1-(3-chloropyridin-2-yl) pyrazol-5-ylcarbonylamino]-5-chloro-N-isopropyl-3-methylbenzamide, etc.

As the neonicotinoid compound represented by the general formula [II], preferred are clothianidin, nitenpyram, imidacloprid, thiacloprid, thiamethoxam, acetamiprid or dinotefuran, etc., with clothianidin being particularly preferable.

The salt of the compound [I] may be any salts, so long as they are agrochemically acceptable salts. Such salts are exemplified by salts to be formed with inorganic bases (e.g., alkali metals, such as sodium, potassium and lithium, etc., alkaline earth metals, such as calcium and magnesium, etc., ammonia and the like), organic bases (e.g., pyridine, triethylamine, triethanolamine, etc.), inorganic acids (e.g., hydrochloric acid, hydrobromic acid, hydroiodic acid, phosphoric acid, sulfuric acid, perchloric acid, etc.) or organic acids (e.g., formic acid, acetic acid, tartaric acid, malic acid, citric acid, oxalic acid, succinic acid, benzoic acid, picric acid, methanesulfonic acid, p-toluenesulfonic acid, etc.).

The compound [I] or a salt thereof can be produced, for example, by the methods described in WO01/070671, WO03/015519 and WO03/016284 or methods similar thereto.

The neonicotinoid compound [II] is the known compound, and clothianidin, nitenpyram, imidacloprid, thiamethoxam, acetaprid, dinotefuran and thiacloprid can be produced, for example, by the methods as described individually in JP-A-Hei 3-157308 (Patent Literature No. 4), JP-A-Hei 2-000171 (Patent Literature No. 5), JP-A-Sho 61-178981 (Patent Literature No. 6), JP-A-Hei 6-183918 (Patent Literature No. 7), JP-A-Hei 4-154741 (Patent Literature No. 8), JP-A-Hei 7-179448 (Patent Literature No. 9) and JP-A-Sho 62-207266 (Patent Literature No. 10), or the similar methods thereto.

In utilizing the compositions of the present invention as an agrochemical preparation, such as insecticides, insecticide-acaricide combinations and fungicide-insecticide combinations, etc., one or not less than two kinds (preferably one kind) of the compounds [I] or their salts and one or two or more kinds (preferably one kind) of the neonicotinoid compounds [II], depending upon the object of use, are dissolved or suspended in a suitable liquid carrier, or are admixed with, or adsorbed on, a suitable solid carrier to thereby be used in the forms which the common agrochemicals can take, namely, by way of the formulations, such as wettable powders, aqueous suspensions, emulsions or emulsifiable concentrates, soluble liquids or solutions, ULV preparations, dusts, granules, tablets, jumbo preparations, pastes, foamable preparations, aerosols, microcapsules, coating preparations for seeds, fumigants, smokes, stick preparations for drenching of crops, or oil preparations, etc. If necessary, these agrochemical preparations may suitably be incorporated with ointment bases, emulsifiers, suspending agents, spreaders, penetrants, wetting agents, dispersing agents, stabilizers, binders, fluidizing auxiliary agents, flocculants, antioxidants, floating agents, anti-foaming agents, anti-freezing agents, preservatives, dehydrating agents, UV absorbers, UV scattering agents, coloring agents or suspension stabilizers, etc., and can be prepared by the procedures known per se. Namely, such preparations can be manufactured by mixing uniformly the compound [I] or its salt and the neonicotinoid compound [II] with a liquid or solid carrier as well as the above-described various additives, etc.

For example, an emulsion or emulsifiable concentrate can be manufactured by mixing for dissolution uniformly the compound [I] or its salt and the neonicotinoid compound [II] as well as an emulsifier and an organic solvent, etc. For example, a granule, a granular wettable powder and the like can be manufactured by mixing uniformly the compound [I] or its salt and the neonicotinoid compound [II], as well as a dispersing agent (surfactant), binder and extender (or solid carrier), etc., followed by granulation. For example, a dust (e.g. a DL dust, etc.) can be manufactured by mixing for pulverizing uniformly the compound [I] or its salt, the neonicotinoid compound [II] and an extender (or solid carrier), etc. For example, a flowable preparation can be manufactured by mixing for dispersion the ingredients, such as the compound [I] or its salt and the neonicotinoid compound [II], a dispersing agent, etc. with use of a stirring machine, followed by wet pulverization with Dyno-Mill, etc. For example, a jumbo preparation can be manufactured by mixing uniformly the compound [I] or its salt, the neonicotinoid compound [II], and a dispersing agent (surfactant), binder, floating agent and extender (or solid carrier), etc., followed by granulation.

Suitable examples of the liquid carrier (e.g., solvents, organic solvents) to be used include solvents, such as water, alcohols (e.g., methyl alcohol, ethyl alcohol, n-propyl alcohol, isopropyl alcohol, ethylene glycol, etc.), ketones (e.g., acetone, methyl ethyl ketone, etc.), ethers (e.g., dioxane, tetrahydrofuran, ethylene glycol monomethyl ether, diethylene glycol monomethyl ether, propylene glycol monomethyl ether, etc.), aliphatic hydrocarbons (e.g., kerosine, paraffin oil, fuel oil, machine oil, etc.), aromatic hydrocarbons (e.g., benzene, toluene, xylene, solvent naphtha, methylnaphthalene, etc.), halogenated hydrocarbons (e.g., dichloromethane, chloroform, carbon tetrachloride, etc.), acid amides (e.g., N,N-dimethylformamide, N,N-dimethylacetamide, etc.), esters (e.g., ethyl acetate, butyl acetate, fatty acid esters of glycerol, etc.) or nitriles (e.g., acetonitrile, propionitrile, etc.), and the like, and these can suitably be used by mixing one or two or more kinds (preferably not less than one but not more than three kinds) in appropriate ratios.

As the solid carrier (i.e., diluents and extenders), vegetable powders (e.g., soybean meal, tobacco meal, wheat flour, wood powder, etc.), mineral powders (e.g., kaolin, bentonite, sepiolite, clays such as acid clay, etc., talc such as talc venetum and powdered talc, etc., silica such as diatomaceous earth and powdered mica, etc., water-soluble materials such as lactose, ammonium sulfate, urea, sodium hydrogencarbonate, sodium thiosulfate, disodium hydrogenphosphate, sodium acetate and sodium carbonate, etc., and the like), calcium carbonate, alumina, powdered sulfur or activated carbon, etc. and these can suitably be used by mixing one or not less than two (preferably not less than one but not more than three kinds) in appropriate ratios.

As the ointment base, for example, there can be appropriately used one or not less than two kinds (preferably not less than one but not more than three kinds) of polyethylene glycol, pectin, polyhydric alcohol esters of higher fatty acids, such as glycerol monostearate, etc., cellulose derivatives, such as methylcellulose, etc., sodium alginate, bentonite, higher alcohols, polyhydric alcohols, such as glycerol, etc., petrolatum, white petrolatum, liquid paraffin, lard, a variety of vegetable oils, lanolin, dehydrated lanolin, hardened oils, resins and the like, or these ointment bases being additionally incorporated with one or two or more kinds (preferably not less than one but not more than four kinds) of the below-described various surfactants.

Referring particularly to the surfactants which are usable as an emulsifier, spreader, penetrant, wetting agent or dispersing agent, etc., the non-ionic surfactants used include, for example, soaps, polyoxyethylene alkylene ethers (New Calgen D1504, Neugen ET65, Neugen ET83, Neugen ET157, etc.), polyoxyethylene alkylaryl ethers (Neugen EA92, Neugen EA142, etc.), polyoxyethylene alkylphenyl ethers, polyoxyethylene nonylphenyl ethers (Nonipol 20, Nonipol 100, etc.), polyoxyethylene polyoxypropylene ethers, polyoxyethylene distyrenated phenyl ether (Neugen EA87, Neugen EA177, etc.), polyoxyethylene alkyl esters (Ionnet MO20, Ionnet MO600, etc.), sorbitan fatty acid esters (Reodol SP-S10, Reodol TW-S20, etc.), polyoxyethylene sorbitan fatty acid esters, block copolymers of ethylene oxide and propylene oxide (Newpole PE64), alkanol amides of higher fatty acids, alkyl maleate copolymers (Demol EP), polyhydric alcohol esters (Tween 20, Tween 80, etc.) and the like, and the cationic surfactants used include, for example, alkylamine salts, quaternary ammonium salts, and the like, while the anionic surfactants used include, for example, high-molecular compounds, such as metal salts of naphthalene sulfonate condensates, naphthalene sulfonate formalin condensates (NewCalgen FS4, etc.), alkylnaphthalene sulfonates (Sorpol 5115, etc.), metal ligninsulfonates, alkylallyl sulfonates and alkylallyl sulfonate sulfates, etc., sodium polystyrenesulfonates, metal salts of polycarboxylic acids, ammonium polyoxyethylene histidylphenyl ether sulfates, higher alcohol sulfonates, higher alcohol ether sulfonates, dialkylsulfosuccinates (NewCalgen EP70P, etc.) or alkali metal salts of higher fatty acids, and the like.

As the stabilizer, use is made of compounds having epoxy groups, antioxidants (e.g., dibutylhydroxytoluene (BHT), butylhydroxyanisole (BHA), tetrakis[3-(3,5-di-tert-butyl-4-hydroxyphenyl)propionyloxymethyl]methane (Irganox 1010), DL-tocopherol, propyl gallate, erysorbic acid, sodium erysorbate, isopropyl citrate, etc.), phosphoric acid, PAP auxiliary agent (isopropyl acid phosphate), cyclodextrin (Toyoderin P), or tall oil fatty acids (Hartall fatty acids), etc., and these can appropriately be used by mixing one or two or more kinds (preferably not less than one but not more than three kinds) of them in suitable ratios.

As the binder, use is made of dextrin, alpha-starch, polyvinyl alcohol, gum arabic, sodium alginate, polyvinylpyrrolidones, glucose, sucrose, mannitol or sorbitol, etc., and these can suitably be used by mixing one or two or more kinds (preferably not less than one but not more than three kinds) of them in appropriate ratios.

As the fluidizing auxiliary agent, use is made of PAP auxiliary agent (e.g., isopropyl acid phosphate), talc, etc., and these can appropriately be used by mixing one or two or more kinds (preferably, not less than one but not more than three kinds) in suitable ratios.

As the anti-coagulating agent, use is made of white carbon, diatomaceous earth, magnesium stearate, aluminum oxide or titanium dioxide, etc., and these can suitably used by mixing one or two or more kinds (preferably, not less than one but not more than three kinds) of them in appropriate ratios.

As the flocculant, use is made of liquid paraffin, ethylene glycol, diethylene glycol, triethylene glycol or isobutylene polymer (e.g., IP Solvent), etc., and these can suitably be used by mixing one or two or more kinds (preferably, not less than one but not more than three kinds) of them in appropriate ratios.

As the antioxidant, use is made of dibutylhydroxytoluene, 4,4-thiobis-6-tert-butyl-3-methylphenol, butylhydroxyanisole, para-octylphenol, mono(or di- or tri-) (α-methylbenzyl) phenol, 2,6-di-tert-butyl-4-methylphenol or tetrakis[3-(3,5-di-tert-butyl-4-hydroxyphenyl)propionyl-oxymethyl]methane, etc. and these can appropriately be used by mixing one or two or more kinds (preferably, not less than one but not more than three kinds) of them in suitable ratios.

The floating agent, which is particularly utilized for the manufacture of jumbo preparations, preferably includes, for example, powdered bases with a specific gravity of not more than 1 (preferably 1 to 0.5), and the like. The said powdered bases are preferably exemplified by those with a particle size of not more than 600 µm, preferably 600 µm to 10 µm; the inorganic ones are naturally-occurring glassy or vitreous materials being provided with one or several independent air bubbles through the burning treatment, and include, for example, perlite composed of perlite and obsidian, Shirasu Balloons (tradename) composed of Shirasu, vermiculite composed of vermiculite rock, etc. as well as Phylite (tradename), or microsized hollow materials based on aluminosilicate as produced through the burning treatment, etc., while the organic ones can be exemplified by higher fatty acids commonly called "waxy substances" which are in the solid state at ambient temperature, such as stearic acid and palmitic acid, as well as higher alcohols, such as stearyl alcohol, paraffin wax and the like. Since such waxy substances are water-repellent and resistant to water-penetration, there develops the likelihood that the active ingredients of agrochemicals tend to be entrapped in such waxy substances over an extended period of time and get difficult to be dispersed into water, and consequently, such active ingredients are preferably used by mixing with the above-described glassy or vitreous hollow materials.

As the anti-foaming agent, use is made of silicone-based anti-foaming agents (e.g., Antifoam E20, etc.) and the like, and these can suitably be used by mixing one or two or more kinds (preferably, not less than one but not more than three kinds) of them in appropriate ratios.

As the anti-freezing agent, use is made of ethylene glycol, diethylene glycol, polyethylene glycol or glycerol, etc., and these can suitably be utilized by mixing one or two or more kinds (preferably, not less than one but not more than three kinds) of them in appropriate ratios.

As the preservative, use is made of butylparaben or potassium sorbate, etc., and these can suitably be used by mixing one or two or more kinds (preferably, not less than one but not more than three kinds) of them in appropriate ratios.

As the dehydrating agent, use is made of anhydrous gypsum, silica gel powders, etc., and these can suitably used by mixing one or two or more kinds (preferably, not less than one but not more than three kinds) of them in appropriate ratios.

As the UV absorber, use is made of 2-(2'-hydroxy-5'-methylphenyl) benzotriazole, 2-ethoxy-2'-methyloxalic acid bisanilide or dimethyl succinate/1-(2-hydroxyethyl)-4-hydroxy-2,2,6,6-tetramethylpiperidine polycondensates, etc., and these can suitably be used by mixing one or two or more kinds (preferably, not less than one but not more than three kinds) of them in appropriate ratios.

As the UV scattering agent, use is made of titanium dioxide, etc., and these can suitably be used by mixing one or two or more kinds (preferably, not less than one but not more than three kinds) of them in appropriate ratios.

As the coloring agent, use is made of Cyaningreen G, Eriogreen B400, etc., and these can suitably be used by mixing one or two or more kinds (preferably, not less than one but not more than three kinds) of them in appropriate ratios.

As the suspension stabilizer, use is made of polyvinyl alcohols (Gohsenol GH17, etc.), clay minerals (e.g., Kunipia F, VEEGUM R, etc.) or silicon dioxide (Aerosil COK84, etc.), etc., and these can suitably used by mixing one or two or more kinds (preferably, not less than one but not more than three kinds) of them in appropriate ratios.

The jumbo preparation, dust, granule, granular wettable powder, wettable powder, etc. may be used after being packed as divided in 20 to 200 g unit portions in bags made of a water-soluble film in order to simplify their application. The said water-soluble film is exemplified by polyvinyl alcohol, carboxymethylcellulose, starch, gelatin, polyvinylpyrrolidone, polyacrylic acid and its salts, Pullulan (tradename: starch-based polysaccharides) or Paogen (tradename: water-soluble thermoplastic polymer), etc.

In manufacturing the composition preparations according to the present invention, it is possible to control the release of both or either one of the active ingredients, as the case may be, to thereby sustain its or their insecticidal effect (s) over a prolonged period of time.

The compound [I] or its salt and the neonicotinoid compound [II] as combined are normally contained in the composition of the present invention at the rate of about 0.1 to 80% by weight based on the total weight of the composition. In cases where they are utilized in the form of, for example, emulsifiable concentrate, soluble liquid, wettable powder (e.g., granular wettable powder), aqueous suspension preparation or microemulsion, etc., they are suitably incorporated into such formulations at the rate in the range of normally about 1 to 80% by weight, preferably about 10 to 50% by weight. In cases where they are utilized in the formulations forms, such as oil solution, dust, etc., they are suitably formulated into such formulations at the rate in the range of normally about 0.1 to 50% by weight, preferably about 0.1 to 20% by weight. When they are used in the formulations forms, such as granule, tablet, jumbo preparation, etc., they are incorporated into such formulations at the rate in the range of normally about 0.5 to 50% by weight, preferably about 0.5 to 10% by weight.

The compound [I] or its salt and the neonicotinoid compound [II] are preferably contained in the composition of the present invention at the rate of 1:0.1 to 1:20 on a weight ratio, more preferably 1:0.2 to 1:10 on a weight ratio.

The contents of additives other than the above-mentioned active ingredients are usually in the range of about 0.001 to 99.9% by weight, preferably about 1 to 99% by weight, though they vary depending upon the type or content of the active ingredients of agrochemicals, or the formulation of agrochemical preparations, etc. More particularly, it is preferred to add, on the basis of the total weight of the composition, a surfactant at rates in the range of normally about 1 to 30% by weight, preferably about 1 to 15% by weight, a fluidizing auxiliary agent at rates in the range of about 1 to 20% by weight, and a carrier at rates in the range of about 1 to 90% by weight, preferably about 1 to 70% by weight, respectively. Specifically, in the case of manufacture of a liquid preparation, it is preferable to add a surfactant at rates in the range of normally about 1 to 20% by weight, preferably 1 to 10% by weight, and water at rates in the range of about 20 to 90% by weight, respectively. In cases where an emulsifiable concentrate is produced, it is desirable to add a surfactant at rates in the range of normally about 1 to 30% by weight, preferably about 2 to 15% by weight, and an organic solvent. In the case of production of a granular wettable powder, it is desired to add a surfactant at rates in the range of normally about 0.1 to 10% by weight, preferably about 0.5 to 5% by weight, and a binder at rates in the range of about 0.1 to 15% by weight, preferably about 0.5 to 5% by weight, respectively, as well as an extender, such as lactose, ammonium sulfate or clay, etc. In cases where a granule is manufactured, it is desirable to add a surfactant at rates in the range of normally about 0.1 to 10% by weight, preferably about 0.5 to 5% by weight, and a stabilizer at rates in the range of about 0.1 to 10% by weight, preferably about 0.5 to 5% by weight, respectively, as well as an extender, such as clay, etc. In the case of production of a jumbo preparation, it is desired to add a surfactant at rates in the range of normally about 0.1 to 15% by weight, preferably about 0.5 to 5% by weight, a binder at rates in the range of about 0.5 to 10% by weight, preferably about 0.5 to 5% by weight, and a floating agent at rates in the range of about 0.5 to 40% by weight, preferably about 1 to 20% by weight, respectively, as well as an extender, such clay, etc.

A wettable powder (e.g., a granular wettable powder) and the like, on the occasion of use, are desirably applied or sprayed after being suitably diluted (e.g., about 100- to 5.000-fold dilution) with water, etc.

Moreover, the composition of the present invention can suitably be used after being incorporated with the active ingredients of agrochemicals other than the compound [I] or its salt and the neonicotinoid compound [II], such as other insecticidal active ingredients, acaricidal active ingredients, fungicidal active ingredients, nematicidal active ingredients, herbicidal active ingredients, plant hormone agents, plant growth regulators, synergists (e.g., piperonyl butoxide, sesamex sulfoxide, MGK 264, N-decylimidazole, WARF-antiresistant, TBPT, TPP, IBP, PSCP, $CH_3I$, t-phenylbutenone, diethyl maleate, DMC, FDMC, ETP, ETN), attractants, repellents or fertilizers, etc.

Below described are examples of the insecticidal active ingredients, acaricidal active ingredients and bactericidal active ingredients which can be incorporated into the compositions of the present invention:

Insecticidal Active Ingredients:

O-Ethyl O-4-nitrophenyl phosphonothioate (EPN), acephate, isoxathion, isofenfos, isoprocarb, etrimfos, oxydeprofos, quinalphos, cadusafos, chlorethoxyfos, chlorpyrifos, chlorpyrifos-methyl, chlorofenvinphos, salithion, cyanophos, disulfoton, dimethoate, sulprofos, diazinon, thiometon, tetrachlorvinphos, tebupirimfos, trichlorphon, naled, vamidothion, pyraclophos, pyridafenthion, pyrimiphos-methyl, fenitrothion, fenthion, phenthoate, butathiofos, prothiofos, propaphos, profenofos, benclothiaz, phosalone, fosthiazate, marathion, methidathion, metolcarb, monocrotophos, phenobcarb (BPMC), 3,5-xylyl N-methylcarbamate (XMC), alanycarb, ethiofencarb, carbaryl, carbosulfan, carbofuran, xylylcarb, cloethocarb, thiodicarb, triazamate, pirimicarb, fenoxycarb, fenothiocarb, furathiocarb, propoxur, bendiocarb, benfuracarb, methomyl, acrinathrin, imiprothrin, ethofenprox, cycloprothrin, sigma-cypermethrin, cyhalothrin, cyfluthrin, cypermethrin, silafluofen, tefluthrin, deltamethrin, tralomethrin, fenvalerate, fenpropathrin, flucythrinate, fluvalinate, flufenprox, fluproxyfen, profluthrin, beta-cyfluthrin, benfluthrin, permethrin, cartap, thiocyclam, bensultap, avermectin, emamectin-benzoate, chlorfluazuron, cyromazine, diafenthiuron, dichlorvos, diflubenzuron, spynosyn, spiromesifen, teflubenzuron, tebufenozide, hydroprene, vaniliprole, pymetrozine, pyriproxyfen, fipronil, flufenoxuron, buprofezin, hexaflumuron, milbemycin, lufenuron, chlorphenapyr, pyridalyl, flufendiamide, SI-0009, metofluthrin, noviflumuron, dimefluthrin, cyflumetofen, pyrafluprole and pyriprole.

Acaricidal Active Ingredients:

Clofentezine, dienochlor, tebufenpyrad, pyridaben, hexythiazox, fenazaquin, fenpyroximate, etoxazole, amitraz, bromopropylate, fenbutatin oxide, pyrimidifen, BPPS (propargite), tebufenpyrad and dicofol.

Fungicidal Active Ingredients:

Iprobenphos (IBP), ampropylfos, edifenphos, chlorthiophos, tolclofos-methyl, fosetyl, ipconazole, imazalil, imibenconazole, etaconazole, epoxiconazole, cyproconazole, diniconazole, difenoconazole, tetraconazole, tebuconazole, triadimenol, triadimefon, triticonazole, triforine, bitertanol, viniconazole, fenarimol, fenbuconazole, fluotrimazole, furconazole-cis, flusilazole, flutriafol, bromuconazole, propiconazole, hexaconazole, pefurazoate, penconazole, myclobutanil, metconazole, cabendazin, debacarb, prothiocarb, benomyl, maneb, TPN, isoprothiolane, iprodione, iminoctadine-albesil, iminoctadine-triacetate, ethirimol, etridiazole, oxadixyl, oxycarboxin, oxolinic acid, ofurace, kasugamycin, carboxin, captan, clozylacon, chlobenthiazone, cyprodinil, cyprofuram, diethofencarb, dichlofluanid, diclomezine, zineb, dimethirimol, dimethomorph, dimefluazole, thiabendazole, thiophanate-methyl, thifluzamide, tecloftalam, triazoxide, triclamide, tricyclazole, tridemorph, triflumizole, validamycin A, hymexazol, pyracarbolid, pyrazophos, pyrifenox, pyrimethanil, pyroquilon, ferimzone, fenpiclonil, fenpropidin, fenpropimorph, fthalide, furametpyr, furalaxyl, fluazinam, furcarbanil, fluquinconazole, fludioxonil, flusulfamide, flutolanil, butiobate, prochloraz, procymidone, probenazole, benalaxyl, benodanil, pencycuron, myclozolin, metalaxyl, metsulfovax, methfuroxam, mepanipyrim, mepronil, kresoxim-methyl, azoxystrobin, methominostrobin (SSF-126), carpropamid, acibenzolar-S-methyl, orysastrobin, pyraclostrobin, benthiabaricarb, ƙ boscalid, metrafenone, fluoxastrobin, proquinazid, flumorph, prothioconazole, penthiopyrad, fluopicolide, amsuldole, SYP-Z071 and MTF-753.

The above-mentioned "other active ingredients of agrochemicals" all are the known active ingredients of agrochemicals. The other active ingredients of agrochemicals may be contained in one or two or more kinds (preferably, not less than one but not more than three kinds) in the compositions.

The compositions of the present invention exhibit an improved degree of safety to mammals and crops, while they possess enhanced insecticidal action against many species of insect pests (inclusive of arthropods other than the class Insecta).

When not less than two kinds of insecticidal compounds are mixed in aiming at an intensified efficacy or a broadened scope of the targeted insect pests to be controlled, generally, investigation is carried out into a novel application by simply adding the application rates determined for their single applications, whereby there is incurred an increased risk of causing chemical injuries. In the combined treatment according to the present invention, the compounds [I] themselves are almost free from their risk of causing chemical injuries, and consequently, the risk of causing chemical injuries to be incurred by such treatment is substantially negligible, in contrast with the treatment through single application of the compound [II]. Because the compositions can produce the synergistic effect, additionally, the application rates of either one or both of the compounds [I] and [II] can be reduced from the ones specified for single uses of these compounds, thereby leading to a by far reduced risk of causing chemical injuries.

The compositions of the present invention are specifically applicable, for example, to the control of the below-described insect pests:

Namely, they are especially effective for controlling the insect pests, which are exemplified by: insect pests of the order Hemiptera, such as *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae, Aphis gossypii, Myzus persicae, Aulacorthum solani, Aphis spiraecola, Bemisia tabaci, Trialeurodes vaporariorum, Sogatella furcifera, Empoasca onukii, Pseudococcus comstocki, Planococcus citri, Icerya purchasi, Plautia stali Eysarcoris parvus* and the like; insect pests of the order Lepidoptera, such as *Spodoptera litura, Plutella xylostella, Pieris rapae crucivora, Chilo suppressalis, Autographa nigrisigna, Helicoverpa assulta, Pseudaletia separate, Mamestra brassicae, Adoxophyes orana fasciata, Notarcha derogate, Cnaphalocrocis medinalis, Phthorimaea operculella, Chilo polychrysus, Typoryza incertulas, Spodoptera exigua, Agrotis segetum, Agrotis ipsilon, Heliothis armigera, Heliothis virescens, Heliothis zea, Naranga aenescens, Ostrinia nubilalis, Ostrinia furnacalis, Parnara guttata, Adoxophyes sp., Caloptilia theivora, Phyllonorycter ringoneella, Carposina niponensis, Grapholita molesta, Cydia pomonella* and the like; insect pests of the order Coleoptera, such as *Epilachna vigintioctopunc tata, Aulacophorafemoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda* and the like; insect pests of the order Diptera, such as *Musca domestica, Culex popiens pallens, Tabanus trigonus, Delia antique, Delia platura, Anopheles sinensis, Agromyza oryzae, Hydrellia griseola, Chlorops oryzae, Dacus cucurbitae, Ceratitis capitata, Liriomyza trifolii* and the like; insect pests of the order Orthoptera, such as *Locusta migratoria, Gryllotalpa Africana, Oxya yezoensis, Oxya japonica* and the like; insect pests of the order Thysanoptera, such as *Thrips tabaci, Thrips parmi, Frankliniella occidentalis, Baliothrips biformis, Scirtothrips dorsalis* and the like; insect pests of the order Hymenoptera, such as *Athalia rosae, Acromyrmex* spp., *Solenopsis* spp. and the like; insect pests of the family Blattodea, such as *Blattella germanica, Periplaneta fuliginosa, Periplaneta japonica, Periplaneta Americana* and the like; nematodes, such as *Aphelenchoides besseyi, Nothotylenchus acris* and the like; termites, such as *Coptotermes formosanus, Reticulitermes speratus, Odontotermes formosanus, Cryptotermes domesticus* and the like, etc.

Also, the compositions of the present invention can find application in the field of treatment of livestock diseases and in the industry of animal husbandry as well as in maintenance of the public hygiene by exterminating arthropoids and parasite insects living in and/or on the bodies of the class Vertebrate, such as humans, cattle, sheep, goats, hogs, poultry, dogs, cats and fishes. Examples of the said parasites include *Aedes* spp., *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., *Phthiraptera* (e.g., *Damalinia* spp., *Linognathus* spp., *Haematopinus* spp.), fleas (e.g., *Ctenocephalides* spp., *Xenosylla* spp., etc.) or *monomorium pharaonis*, and the like.

The compositions of the present invention show an extremely low toxicity and can be used as an excellent agrochemical composition.

For example, the compositions of the present invention can be sprayed over paddy fields, fields, fruit tree orchards, non-cultivated waste lands, houses, etc. by use of the per se known methods to thereby exterminate the above-mentioned living insect pests (injurious insects) by allowing such insect pests to contact with or ingest them. In another embodiment of the present invention, for example, the compositions of the present invention can be administered to vertebrates internally (in the body) or externally (on the body surface) to thereby exterminate the arthropods parasitic on such vertebrate or parasites.

With reference to the particular application method for the combination preparations comprising the composition of the present invention, use can be made of the same methods as the ordinary agrochemical application methods. Also, the preparations each containing a single different active ingredient can find application through blending on the occasion of use. The application method for such agrochemical preparations can be exemplified by the foliage application, trunk or bark application, ULV application, granule foliar-application, land or soil application, soil drenching, water-surface application, soil incorporation, nursery bed incorporation, seedling-raising box treatment, nursery bed treatment, plant foot treatment, planting furrow treatment, planting row treatment, side row treatment, trunk or bark drenching, trunk or bark spreading, seed coating or dressing, seed immersion or soaking, poison bait, fertilizer incorporation or water blending or mixing for irrigation, etc., but are not understood to be limited to them. The application time for the combination preparations comprising the composition of the present invention or mixtures of the preparations each containing a single different active ingredient may be any arbitrary occasions in advance of planting in the case of treatment of seeds, seed potatoes or bulbs, etc.; and may be the occasions of sowing, seedling-raising or seedling planting for the improved efficacy, although it can be any occasion during the vegetation period after seedling planting, in the case of treatment of the soil; and may be any occasions during the seedling raising period and during the vegetation period on the farm field in the case of foliar application or spraying.

In cases where sowing is effected on the nursery soil for seedling raising into which the combination preparations comprising the composition of the present invention or mixtures of the formulations each comprising a single different active have been incorporated, when provisional planting is done with use of the said nursery bed soil, or in cases where the soil is treated through solution drenching or granule application during the seedling raising period, all the insect pests appearing during the seedling raising period can also be exterminated.

As the application method on the occasion of seedling planting, treatment can be conducted through soil incorporation on the whole surface of the field or on furrows in advance of planting, while treatment can also be done by granule application or solution drenching into planting holes. After planting, furthermore, treatment can be effected by immediately applying a granule or drenching a solution at plant foots.

The crop to be raised by seedling in the farm field is able to be subjected not only to seed treatment, but also soil incorporation treatment on the whole surface of the field or on the furrows in advance of planting.

The compositions of the present invention, through their mixed use with natural-enemy microbial formulations, their combined utilization with natural-enemy organisms (e.g., natural enemy insects, such as parasitic bees and predacious beetles, predacious acarides, parasitic nematodes, insect-pathogenic microbes, etc.), their combined use with insect pheromones, their combined employment with genetically modified crops, their combined utilization with attractants and repellents, and the like, can contribute to promotion of the IMP (Integrated Pest Management).

Taking for example the control of diamond-back moths by way of the disturbance in signal communication through use of the pheromones or with utilization of the natural enemies in the cultivation of cabbages, such controlling methods are known to be less effective or entirely ineffective, when the population density of the injurious insect to be controlled becomes high. In the farm filed where the population density of diamond-back moths is suppressed to an extremely lower level through soil treatment with the composition of the present invention conducted on the occasion of planting of cabbages, at the point of time when the compound [I] or its salt, or the neonicotinoid compound [II] starts to lose its residual effect, the disturbance in signal communication or the utilization of the natural enemies can be employed to thereby secure by far the originally intended effect of such signal communication disturbance or the natural-enemy utilization, thus ensuring that the pest control would keep on working over a prolonged period of time. In controlling insect pests by way of the disturbance in signal communication through use of the pheromones or with utilization of the natural enemies, moreover, the problem arises with proliferation of injurious insects other than the targeted one to be controlled. Under these circumstances, the compositions of the present invention can be applied to thereby suppress the proliferation of injurious insects other than the targeted one, which proliferation has been the problem of great concern in the control of insect pests by way of the disturbance in signal communication or with utilization of natural enemies, and can therefore provide the by far improved integrated pest control.

The application rate of the compositions of the present invention can be varied over a widened range, depending for example upon the time, location and method of application, etc. but the application is desirably effected at rates of about 0.3 to 3,000 g, preferably about 50 to 1,000 g, of the active ingredient (the total sum of the amounts of the compound [I] or its salt and the neonicotinoid compound [II]) per hectare. In cases where the composition of the present invention is formulated into the form of wettable powder, it is desirable to make application after being diluted to a final concentration of the active ingredient (the total sum of the concentrations of the compound [I] or its salt and the neonicotinoid compound [II]) of about 0.1 to 1,000 ppm, preferably about 10 to 200 ppm, for foliage application, and about 1 to 10,000 ppm, preferably about 100 to 2,000 ppm, for drenching into the soil.

EXAMPLES

Hereunder, the present invention is illustrated in more detail by reference to the following Examples and Test Examples.

In the Examples described below, the Compounds (I-1), (I-2), (I-3), (I-4), (I-5) and (I-6) are understood to designate 2-[1-(3-chloropyridin-2-yl)-3-trifluoromethylpyrazol-5-yl-carbonylamino]-N-isopropyl-3-methylbenzamide, 5-chloro-2-[1-(3-chloropyridin-2-yl)-3-trifluoromethylpyrazol-5-yl-carbonylamino]-N-isopropyl-3-methylbenzamide, 2-[1-(3-chloropyridin-2-yl)-3-chloropyrazol-5-ylcarbonylamino]-N-isopropyl-3-methylbenzamide, 5-chloro-2-[1-(3-chloropyridin-2-yl)-3-chloropyrazol-5-ylcarbonylamino]-N-isopropyl-3-methylbenzamide, 2-[3-bromo-1-(3-chloropyridin-2-yl)pyrazol-5-ylcarbonylamino]-N-isopropyl-3-methylbenzamide and 2-[3-bromo-1-(3-chloropyridin-2-yl)-pyrazol-5-ylcarbonylamino]-5-chloro-N-isopropyl-3-methylbenzamide, respectively.

Example 1

5 parts of the Compound (I-1), 8 parts of clothianidin, 0.5 part of a non-ionic surfactant (tradename: Noigen EA-177; manufactured by Dai-ichi Kogyo Seiyaku CO., Ltd.), 2 parts of an anionic surfactant (tradename: New Calgen FS-4; manufactured by Takemoto Oils & Fats Co. Ltd.), 2 parts of polyvinyl alcohol (tradename: Gohsenol GH-17; manufactured by Nippon Synthetic Chemical Co., Ltd.), 0.1 part of butylparaben and 82.4 parts of water are mixed and dispersed sufficiently with a high-speed stirring machine, followed by wet pulverization (1 pass) with a pulverizer, "Dyno-Mill" (constructed by Sinmaru Enterprise Co., 1.0 mm glass beads, 80% of filing factor, 15 m/sec of peripheral speed), to give a flowable preparation.

Example 2

5 parts of the Compound (I-2), 8 parts of clothianidin, 0.5 part of a nonionic surfactant, Noigen EA-177, 1.5 parts of an anionic surfactant, New Calgen FS-4, 2 parts of silicon dioxide (tradename: Aerosil COK84; manufactured by Nippon Aerosil Co., Ltd.), 2 parts of polyvinyl alcohol (tradename: Gohsenol GH-17), 7 parts of ethylene glycol, 0.2 part of a silicone-based anti-foaming agent (tradename; Antifoam E-20; manufactured by Kao Corp.), 0.1 part of butylparaben and 73.7 parts of water are mixed and dispersed sufficiently with a high-speed stirring machine, followed by wet pulverization (1 pass) with a pulverizer, "Dyno-Mill" (constructed by Sinmaru Enterprise Co., 1.0 mm glass beads, 80% of filling factor, 15 m/sec of peripheral speed), to give a flowable preparation.

Example 3

1 part of the Compound (I-1), 1 part of clothianidin, 0.5 part of a non-ionic surfactant (tradename: New Pole PE-64; manufactured by Sanyo Chemical Industries Ltd.), 4 parts of alpha-starch and 93.5 parts of clay are mixed uniformly, and the mixture is admixed with 5 to 10 parts of water, kneaded and followed by extrusion through a 0.8 mm-4-screen to conduct granulation. The resultant granulated material is dried at 60° C. for 1 hour to give a granule preparation.

Example 4

A solution of 20 parts of nitenpyram and 80 parts of cyclodextrin (tradename: Toyoderin P; manufactured by JT Foods Co., Ltd.) in 400 parts of water is spray-dried to give a cyclodextrin clathrate A of nitenpyram.

1 part of the Compound (I-2), 5 parts of cyclodextrin clathrate A, 2 parts of an anionic surfactant (tradename: New Calgen EP-70P; manufactured by Takemoto Oils & Fats Co., Ltd.), 10 parts of dextrin NDS and 82 parts of clay are mixed uniformly, and the mixture is kneaded with 5 to 10 parts of water, and the same procedure as described in Example 2 is followed to give a granule preparation.

Example 5

0.2 part of the Compound (I-1), 0.15 part of clothianidin, 2 parts of an anionic surfactant, New Calgen EP-70P, 0.2 part of a flocculant, IP Solvent, 1 part of white carbon and 96.45 parts of clay are kneaded uniformly, followed by fine pulverization to give a DL dust preparation.

Example 6

0.2 part of the Compound (I-1), 1.25 parts of the cyclodextrin clathrate A prepared in Example 4, 2 parts of an anionic surfactant, New Calgen EP-70P, 0.2 part of a flocculant, IP Solvent, 1.5 parts of white carbon and 94.85 parts of clay are kneaded uniformly, followed by fine pulverization to give a DL dust preparation.

Example 7

0.2 part of the Compound (I-2), 0.15 part of imidacloprid, 1 part of tall oil fatty acid (tradename: Hartall FA-1; manufactured by Harima Chemicals, Inc.), 0.2 part of a flocculant, IP Solvent, 1.5 parts of white carbon and 95.1 parts of clay are kneaded uniformly, followed by fine pulverization to give a DL dust preparation.

Example 8

5 parts of the Compound (I-4), 8 parts of clothianidin, 7 parts of an anionic surfactant (tradename: NewCalgen 98147TX; manufactured by Takemoto Oils & Fats Co., Ltd.) and 80 parts of N-(n-dodecyl)pyrrolidone (tradename: AGSOLEX12; manufactured by ISP TECHNOLOGIES INC.) are mixed uniformly for dissolution to give an emulsifiable concentrate.

Test Example 1

Insecticidal Effect Against *Spodoptera litura* by Soaking Treatment of a Bait Crop Plant A test compound was dissolved by addition of acetone containing 5% of Tween 20 (tradename) at the rate of 0.1 ml per 1 mg of the test compound, and after the solution is diluted with aqueous 5,000-fold diluted DAIN solution to a predetermined concentration, soybean leaves after complete development of primary leaves were treated through soaking in the insecticide solution for several seconds. After the insecticide solution was dried, four primary leaves were cut off and placed in an ice-cream cup (with a capacity of 180 ml), in which 10 heads of 3-instra larvae of *Spodoptera litura* were released. The ice-cream cup was kept in a breeding room controlled at a constant temperature (25° C.), and the number of dead larvae was counted three days later. The death rate of larvae was calculated by the following equation, and the results were shown in Table 1.

$$\text{Death rate of larvae} = (\text{Number of larvae dead})/(\text{Number of larvae tested}) \times 100 \quad \text{[Equation 1]}$$

TABLE 1

Insecticidal effect in soybean plants against *Spodoptera litura* through soaking treatment of leaves

| Compound | Compound Concentration (ppm) | Death rate, 3 days later, % | |
|---|---|---|---|
| Compound (I-2) | 0.03 | 30 | |
| Clothianidin | 0.03 | 0 | |
| Compound (I-2) + clothianidin | 0.03 + 0.03 | 70* | 30** |

Notes:
*Activity found by the combination of two kinds of the compounds (actual effect)
**Activity calculated by Colby's equation (expected effect)

When the effect obtained by combination of two kinds of the active compounds exceeds the expected value E as calculated by the below-described equation of Colby et al., the synergistic effect is deemed to exist.

$$E = X + Y - X \cdot Y/100 \quad \text{[Equation 2]}$$

wherein
E=the death rate of larvae obtained when the active compounds A and B are used at the dose of m and n, respectively;
X=the death rate of larvae when the active compound A is used at the dose of m;
Y=the death rate of larvae when the active compound B is used at the dose of n.

As is indicated in Table 1, the Compound (I-2), when used as a mixture with clothianidin, was found to produce a greater insecticidal effect than would be expected when individually used alone.

Test Example 2

Insecticidal Effect Against *Spodoptera litura* Through Soaking Treatment of Roots of a Bait Crop Plant A test compound was dissolved by adding acetone containing 5 of Tween 20 (tradename) at the rate of 0.1 ml per 1 mg of the test compound, and the insecticide solution prepared by diluting the solution with ion-exchange water to a predetermined concentration was charged into a light-shielded Erlenmeyer flask (100 ml), into which the root portion of a soybean plant in the stage of development of primary leaves was soaked after being washed with running water to remove soil. Five days after root soaking, two primary leaves were cut off and placed in an ice-cream cup (with a capacity of 180 ml), into which 10 heads of 3-instar larvae were released. The ice-cream cup was kept in a breeding room controlled at a constant temperature (25° C.), and 5 days later, the number of dead larvae was counted. The death rate of larvae was calculated by the following equation, with the results being tabulated in Tables 2 and 3.

$$\text{Death rate of larvae} = (\text{Number of larvae dead})/(\text{Number of larvae tested}) \times 100 \quad \text{[Equation 3]}$$

TABLE 2

Insecticidal effect in soybean plants against *Spodoptera litura* through soaking treatment of roots

| Compound | Compound Concentration (ppm) | Death rate, 5 days later, % | |
|---|---|---|---|
| Compound (I-1) | 0.007 | 55 | |
| Thiamethoxam | 0.007 | 0 | |
| Compound (I-1) + thiamethoxam | 0.007 + 0.007 | 80* | 55** |

Notes:
*Activity found by the combination of two kinds of the compounds (actual effect)
**Activity calculated by Colby's equation (expected effect)

TABLE 3

| Compound | Compound Concentration (ppm) | Death rate, 5 days later, % | |
|---|---|---|---|
| Compound (I-6) | 0.00032 | 0 | |
| Clothianidin | 0.00032 | 0 | |
| Compound (I-6) + clothianidin | 0.00032 + 0.00032 | 65* | 0** |

As is indicated in Table 2, the Compound (I-1), when used as a mixture with thiamethoxam, was found to produce a greater insecticidal effect than would be expected when individually used alone, and the synergistic effect due to the mixing was observed.

As is indicated in Table 3, the Compound (I-6), when used as a mixture with clothianidin, was found to produce a greater insecticidal effect than would be expected when individually used alone, and the synergistic effect due to the mixing was observed.

Test Example 3

Insecticidal Effect Against *Chilo suppressalis* Through Drenching Treatment of the Soil with the Insecticide Solution A test compound was dissolved by adding acetone containing 5% of Tween 20 (tradename) at the rate of 0.1 ml per 1 mg of the test compound, and the insecticide solution prepared by diluting the solution with ion-exchange water to a predetermined concentration was drenched onto the surface of the soil for raising rice seedlings (5 to 6 seedlings/plant as planted in a paper pot) in the 2.5- to 3-leaf stage at the rate of 1 ml per plant. Two days later, the stalks about 2 cm higher above the soil surface were cut and placed in a test tube, into which 10 heads of 3-instar larvae of *Chilo suppressalis* were released. The test rube was kept in a breeding chamber controlled at a constant temperature (25° C.), and the number of living larvae was counted 4 to 5 days later. The death rate of larvae was calculated by the following equation, and the results were shown in Tables 4 and 5.

$$\text{Death rate of larvae} = (\text{Number of larvae dead})/(\text{Number of larvae tested}) \times 100 \quad \text{[Equation 4]}$$

TABLE 4

Insecticidal effect in rice plants against *Chilo suppressalis* through drenching treatment of the soil with the insecticide solution

| Compound | Amount applied mg/plant | Death rate, 4 days later, % | |
|---|---|---|---|
| Compound (I-1) | 0.01 | 30 | |
| Clothianidin | 0.001 | 10 | |
| Compound (I-1) + clothianidin | 0.01 + 0.001 | 70* | 37** |

Notes:
*Activity found by the combination of two kinds of the compounds (actual effect)
**Activity calculated by Colby's equation (expected effect)

TABLE 5

| Compound | Amount applied mg/plant | Death rate, 5 days later, % | |
|---|---|---|---|
| Compound (I-5) | 0.15 | 5 | |
| Dinotefuran | 0.44 | 0 | |
| Compound (I-1) + Dinotefuran | 0.15 + 0.44 | 55* | 5** |

Notes:
*Activity found by the combination of two kinds of the compounds (actual effect)
**Activity calculated by Colby's equation (expected effect)

As is indicated in Table 4, the Compound (I-1), when used as a mixture with clothianidin, was found to produce a greater insecticidal effect than would be expected when individually used alone, and the synergistic effect due to the mixing was observed.

As is indicated in Table 5, the Compound (I-5), when used as a mixture with dinotefuran, was found to produce a greater insecticidal effect than expected when individually used alone, and the synergistic effect due to the mixing was observed.

Test Example 4

Insecticidal Effect Against *Plutella xylostella* Through Drenching Treatment of the Soil with the Insecticide Solution A test compound was dissolved by adding acetone containing 5% of Tween 20 (tradename) at the rate of 0.1 ml per 1 mg of the test compound, and the solution was diluted with ion-exchange water to a total volume of 3 ml. Each of the insecticide solutions prepared was drenched onto the surface of the plant root soil for a cabbage plant grown in a cell tray (with a soil capacity of 24 ml). Four days later, the above-ground part of the plant was cut and placed in a plastic cup, into which 10 heads of 2-instar larvae of *Plutella xylostella* were released. The cup was kept in a breeding chamber controlled at a constant temperature (25° C.), and the number of living larvae was counted 4 days later. The death rate of larvae was calculated by the following equation, and the results were shown in Tables 6 and 7.

$$\text{Death rate of larvae} = (\text{Number of larvae dead})/(\text{Number of larvae tested}) \times 100 \quad \text{[Equation 5]}$$

TABLE 6

Insecticidal effect in cabbage plants against *Plutella xylostella* through plant-root drenching treatment with the insecticide solution

| Compound | Amount applied mg/plant | Death rate, 4 days later, % | |
|---|---|---|---|
| Compound (I-2) | 0.0016 | 0 | |
| Dinotefuran | 0.0016 | 0 | |
| Compound (I-2) + dinotefuran | 0.0016 + 0.0016 | 60* | 0** |

Notes:
*Activity found by the combination of two kinds of the compounds (actual effect)
**Activity calculated by Colby's equation (expected effect)

TABLE 7

| Compound | Amount applied mg/plant | Death rate, 4 days later, % | |
|---|---|---|---|
| Compound (I-3) | 0.04 | 50 | |
| Dinotefuran | 0.04 | 10 | |
| Compound (I-3) + dinotefuran | 0.04 + 0.04 | 80* | 55** |

Notes:
*Activity found by the combination of two kinds of the compounds (actual effect)
**Activity calculated by Colby's equation (expected effect)

As is indicated in Table 6, the Compound (I-2), when used as a mixture with dinotefuran, was found to produce a greater insecticidal effect than would be expected when individually used alone, and the synergistic effect due to the mixing was observed.

As is indicated in Table 7, the Compound (I-3), when used as a mixture with dinotefuran, was found to produce a greater insecticidal effect than would be expected when individually used alone, and the synergistic effect due to the mixing was observed.

Test Example 5

Insecticidal Effect Against *Plutella xylostella* Through Soaking Treatment of the Bait Crop A test compound was dissolved by adding acetone containing 5% of Tween 20 (tradename) at the rate of 0.1 ml per 1 mg of the test compound, and the insecticide solution was prepared by diluting the solution with an aqueous 5.000-fold diluted DAIN solution to a predetermined concentration. A cabbage leaf was cut off at the site of petiole and soaked in the insecticide solution for several seconds. After the solution was dried, the leaf was placed in an ice-cream cup (with a capacity of 180 ml), into which 10 heads of 2-instar larvae of *Plutella xylostella* were released. The cup was kept in a breeding room controlled at a constant temperature (25° C.), and the number of dead larvae was counted 4 days later. The death rate of larvae was calculated by the following equation, and the results were shown in Table 8:

(Death rate of larvae=(Number of larvae dead)/(Number of larvae tested)×100     [Equation 6]

TABLE 8

| Compound | Amount applied mg/plant | Death rate, 4 days later, % | |
|---|---|---|---|
| Compound (I-4) | 0.0064 | 15 | |
| Thiamethxam | 0.0064 | 10 | |
| Compound (I-4) + thiamethxam | 0.0064 + 0.0064 | 50* | 23.5** |

Notes:
*Activity found by the combination of two kinds of the compounds (actual effect)
**Activity calculated by Colby's equation (expected effect)

As is indicated in Table 8, the Compound (I-4), when used as a mixture with thiamethxam, was found to produce a greater insecticidal effect than would be expected when individually used alone, and the synergistic effect due to the mixing was observed.

INDUSTRIAL APPLICABILITY

The compositions of the present invention can be utilized as an insecticide for agricultural and horticultural uses.

The invention claimed is:

1. A method for controlling an insect pest, comprising applying an effective amount of an insecticide composition comprising
   (i) at least one compound selected from compounds of formula [Ia],

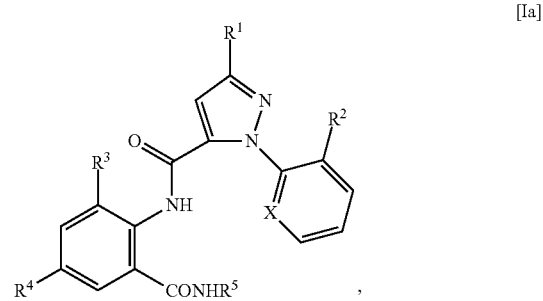

[Ia]

wherein $R^1$ is a halogen atom or a trifluoromethyl group, $R^2$ is a chlorine atom, $R^3$ is a methyl group, $R^4$ is a hydrogen atom or a chlorine atom, $R^5$ is a $C_{1-3}$ alkyl group, and X is N, or a salt thereof, and (ii) dinotefuran, on soil of a farm field through a drenching treatment, a planting-hole treatment, a planting-hole treated soil incorporation, a plant-root treatment or a plant-root treated soil incorporation during a period ranging from a seedling planting time to a vegetation period for a crop to be cultivated by a seedling-planting method.

2. An insecticide composition comprising:
   (i) at least one compound selected from compounds of formula [Ia],

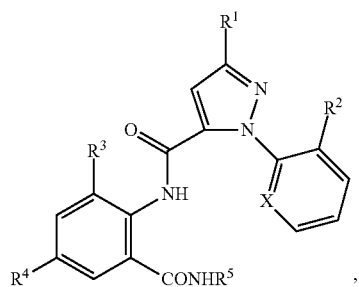 [Ia]
wherein
R¹ is a halogen atom or a trifluoromethyl group,
R² is a chlorine atom,
R³ is a methyl group,
R⁴ is a hydrogen atom or a chlorine atom,
R⁵ is a $C_{1-3}$ alkyl group, and
X is N,
or a salt thereof, and
(ii) dinotefuran.
* * * * *